United States Patent [19]

Baker et al.

[11] Patent Number: 4,808,408

[45] Date of Patent: Feb. 28, 1989

[54] MICROCAPSULES PREPARED BY COACERVATION

[75] Inventors: Richard W. Baker, Palo Alto, Calif.; Yasuo Ninomiya, Ibaraki, Osaka, Japan

[73] Assignee: Bend Research, Inc., Bend, Oreg.

[21] Appl. No.: 770,004

[22] Filed: Aug. 26, 1985

Related U.S. Application Data

[63] Continuation-in-part of Ser. No. 493,706, May 11, 1983, abandoned.

[51] Int. Cl.⁴ ............... H01N 25/34; A61K 9/50; B01J 13/02
[52] U.S. Cl. ............... 424/408; 71/DIG. 1; 264/4.1; 264/4.3; 264/4.32; 424/418; 424/419; 424/492; 424/496; 424/499; 424/500; 424/DIG. 10; 427/213.33; 428/402.2
[58] Field of Search ............... 264/4.1, 4.3, 4.32; 428/402.2; 424/DIG. 10, 408, 418, 419, 492, 496; 427/213.33

[56] References Cited

U.S. PATENT DOCUMENTS

| | | | |
|---|---|---|---|
| 3,038,836 | 6/1962 | Woodard et al. | 424/455 |
| 3,043,782 | 7/1962 | Jensen | 428/402.24 X |
| 3,565,559 | 2/1971 | Sato et al. | 264/4.3 X |
| 3,956,172 | 5/1976 | Saeki et al. | 424/492 X |
| 4,298,612 | 11/1981 | McGovern et al. | 424/DIG. 10 |

FOREIGN PATENT DOCUMENTS

| | | | |
|---|---|---|---|
| 929406 | 6/1963 | United Kingdom | 264/4.3 |
| 1188957 | 4/1970 | United Kingdom | 424/492 |

*Primary Examiner*—Richard D. Lovering
*Attorney, Agent, or Firm*—Chernoff, Vilhauer, McClung & Stenzel

[57] ABSTRACT

There is disclosed an improved complex coacervation process for microencapsulation of core ingredients that are partially soluble in the microcapsule walls wherein the core ingredient is first mixed with a coacervation adjacent prior to forming a first colloidal emulsion of core ingredient, and, after combining the first emulsion with a second colloidal solution and cooling to cause gelation, a water-soluble wax derivative is added. No pH adjustment or dilution is necessary, and very high yields of non-agglomerated microcapsules are obtained, both in terms of quantity of microcapsules and content of core ingredient. When deet is the core ingredient there is obtained a long-lasting mosquito repellent.

8 Claims, No Drawings

MICROCAPSULES PREPARED BY COACERVATION

This is a continuation-in-part of U.S. application Ser. No. 493,706, filed May 11, 1983, now abandoned.

BACKGROUND OF THE INVENTION

Microencapsulation by both simple and complex coacervation is known. U.S. Pat. No. 2,800,457 discloses the basic process of complex coacervation including the steps of (1) emulsifying an oily core ingredient in an aqueous solution of a first colloid, (2) mixing the emulsion with an aqueous solution of a second colloid having opposite electrical charge to that of the first colloid, (3) causing coacervation of the colloids around the oil droplets by dilution with water or by pH adjustment, (4) cooling the mixture to about 0° C. to 10° C. to cause gelation of the coacervate, and (5) hardening the gelled coacervate by pH or temperature adjustment or by treatment with aldehydes. U.S. Pat. No. 3,341,466 discloses a complex coacervation process enabling production of large microcapsules with thick walls. U.S. Pat. No. 3,549,555 discloses a simple coacervation process for encapsulation of oil-in-water emulsions. U.S. Pat. No. 3,956,172 discloses a complex coacervation process wherein the microcapsules are hardened rapidly, without yellowing, and without an increase in the viscosity of the microencapsulation mixture. British Patent No. 929,406 discloses a method of increasing the hardness and decreasing the premeability of microcapsules by treating them with trivalent iron salts and gallic, digallic or tannic acids, using polyoxyethylene sorbitan monostearate in concentrations well below 1% as a surfactant to oppose the tendency of the microcapsules to aggregate.

However, owing to phase inversion, the requirement for dilution and for proper pH, all of the foregoing processes suffer from the drawbacks of requiring constant attention and adjustment of stirring conditions, solution viscosity, pH, and temperature, often producing microcapsules with a significant degree of agglomeration. Furthermore, such prior art processes are particularly unsatisfactory for the production of microcapsules of certain core ingredients that are appreciably soluble in the capsule wall material such as the mosquito repellent, N,N-diethyl-m-toluamide (deet). Typically, microcapsules of such core ingredients are weak, and are composed of less than 50% by dry weight of the core ingredient. In addition, such microencapsulation processes have a poor yield of core ingredient, with typically only about 10% to 40% of the core ingredient being encapsulated.

What is needed, therefore, is a simple highyield microencapsulation process capable of producing stable, relatively high-core-content microcapsules rapidly and without agglomeration, especially with respect to core ingredients that are appreciably soluble in the microcapsule wall material.

SUMMARY OF THE INVENTION

According to the present invention, there are provided an improved and simplified microencapsulation process, microcapsules obtained from such a process, and a long-lasting mosquito repellent composition containing such microcapsules. The process of the present invention is a complex coacervation process differing from the prior art by the use of the essential, additional steps of (1) mixing an ionizable colloid, ionic surfactant, or ionizable long-chain organic compound (collectively referred to hereinafter as a "coacervation adjuvant") with the core ingredient prior to emulsification of the core ingredient in a first aqueous colloid solution; and (2) adding from about 5% to about 20% by weight of a water-soluble wax derivative after gelation and prior to hardening, these two steps being conducted in the absence of any phase inversion, in the absence of any dilution, in the absence of the addition of any inorganic salt, and without the necessity of any pH adjustment.

The first of the two novel steps results in both (1) rapid and efficient coacervation without pH adjustment or dilution, and (2) effective gelation at more moderate temperatures than heretofore possible. The second novel step prevents agglomeration of the capsules, which is particularly severe when the core ingredient has an appreciable solubility in the capsule wall material, and produces stable microcapsules composed of more than 60% by dry weight of the core ingredient with yields of more than 60% of the core ingredient.

DETAILED DESCRIPTION OF THE INVENTION

The complex coacervation process of the present invention comprises the following steps:

(1) mixing a coacervation adjuvant with the core ingredient;

(2) emulsifying the mixture in an aqueous solution of an ionizable colloid;

(3) combining, while agitating, the emulsion of the first step with an aqueous solution of a second ionizable colloid of opposite electrical charge to that of the first colloid;

(4) cooling the mixture to cause gelation of the capsule walls;

(5) adding a water-soluble wax derivative to stabilize the gelled capsules and to prevent agglomeration; and (6) hardening the capsule walls.

All of the above steps are accomplished without dilution, without phase inversion, without the addition of any inorganic salt, and without pH adjustment, resulting in a much simpler and more efficient process than previously known, while at the same time providing extremely high yields of microcapsules having core ingredients with appreciable solubility in the microcapsule walls.

The function of the coacervation adjuvant is to help molecules of the first ionizable colloid to attract oppositely-charged molecules of the second ionizable colloid. The coacervation adjuvant may be (1) an ionizable colloid, such as gelatin, gum arabic, casein, carrageenan, carboxymethylcellulose, and the like; (2) a long-chain ionizable surfactant, preferably with a low hydrophile/lipophile balance (HLB) value in the range of 1 to 8, such as long-chain amines, long-chain polyamines, quaternary ammonium salts, long-chain sulfonic acid salts, long-chain carboxylic acid salts, and the like; or (3) a long-chain ionizable organic compound, such as fatty acids, fatty alcohols and fatty esters.

The core ingredient should be a generally hydrophobic liquid, which may consist of a pure liquid, a mixture of miscible liquids, one or more solids dissolved in a liquid, or an emulsion of a hydrophilic liquid or solution in a hydrophobic liquid. Examples include the mosquito repellent deet, other insect repellents, insect pheromones, insecticides, herbicides, fertilizers, pharmaceuticals, fragrances, flavors, sweeteners, cosmetics, and reactive chemicals. The process is especially useful for encapsulating core ingredients that are difficult to encapsulate by previously known techniques, such as deet, certain other amides, amines, carboxylic acids, aromatic compounds, and, in general, polar organic compounds.

The ionizable colloids should be selected from known colloidal substances such as gelatin, gum arabic, gum karaya, gum tragacanth, casein, carrageenan, and carboxymethylcellulose, such that one colloid is of opposite electrical charge to the other. Preferred colloids are gelatin and gum arabic.

The water-soluble wax derivatives should be present in an amount from about 5% to about 20% by weight, preferably from about 7% to about 15%, and is selected from natural or synthetic wax derivatives, such as derivatives of any of the following: lanolin, carnauba, beeswax, paraffin, polyether-esters, and chlorinated naphthalenes. A preferred example is ethoxylated lanolin.

Referring to the six-step process of the present invention described above, the first two steps may be conducted at ambient temperature or at a higher temperature, such as 35° C. to 50° C. The third step should be conducted at a temperature higher than the gelling point of the colloids, typically between about 35° C. and 50° C. Mixing times are not critical and may be widely varied. Improved, stronger microcapsule walls may be obtained when the emulsion from the first step is subjected to a vacuum to remove dissolved and entrained air. In the fourth step, the mixture should be cooled to about 20° C. or below, preferably between 15° C. and 20° C. Again, the rate of cooling is not critical and may be widely varied with no adverse consequences. The fifth step should be conducted at this cooled temperature. The sixth step may be accomplished by adding an aldehyde, such as formaldehyde, glutaraldehyde, glyoxal, or combinations of these, as described in the above-mentioned patents and in the literature, and raising the temperature gradually to between 20° C. and 40° C. to hasten the hardening process.

Alternatively, hardening may be accomplished by adding one or more hardening agents selected from the aldehydes mentioned above and tannic acid at a temperature of 15° C. to 25° C., followed by allowing the mixture to stand at room temperature for several hours. The tannic acid may be added before or after the water-soluble wax derivative. In the case where tannic acid is used without an aldehyde, the capsules obtained are stable only at temperatures up to about 30° C., melting at higher temperatures, which feature may be useful in the delivery of agents which are biologically or chemically active at temperatures above 30° C. and not at lower temperatures.

EXAMPLES

Example 1

14 g gelatin (Type 2503, Knox Gelatine, Inc., Cherry Hill, New Jersey) was dissolved in 175 ml water at 40° C. A solution of 4.2 g stearic acid in 100 ml deet was emulsified in the gelatin solution by stirring at 40° C. A solution of 9.3 g gum arabic (G-85, MCB Chemicals, Norwood, Ohio) in 135 ml water was added to the emulsion, which was then cooled to 18° C. with continuous stirring for 3 hours. 140 ml of a 30 wt% solution, or 9.3 wt%, of ethoxylated lanolin (Ethoxylan 100, Emery Industries, Inc., Linden, New Jersey) in water was then added, followed 10 minutes later by addition of 735 μl of 50 vol% glutaraldehyde in water. The solution was stirred slowly for 1.5 hours and allowed to stand overnight at room temperature. The microcapsule precipitate was then centrifuged at 2800 rpm for 15 minutes to recover the microcapsules. Approximately 220 ml of non-agglomerated microcapsules that contained 42% to 44% by wet weight deet were obtained. By drying the microcapsules for four hours at room temperature, the deet content was determined to be 75% to 80% by dry weight. The yield of microencapsulated deet was approximately 94%. In this example, gelatin, which had a negative electrical charge, ws the first ionizable colloid; stearic acid, which also had a negative electrical charge, was the coacervation adjuvant; deet was the core ingredient; gum arabic, which had a positive electrical charge, was the second ionizable colloid; and ethoxylated lanolin was the water-soluble wax derivative.

Example 2

20 g gelatin (Type 2503) was dissolved in 200 ml water at 45° C. A dispersion of 8 g gum arabic (G-85) in 80 ml deet was added to the gelatin solution and emulsified by vigorous stirring at 45° C. A solution of 20 g gum arabic in 200 ml water was added to the emulsion with stirring. The mixture was then cooled to 25° C. with continuous stirring. A solution of 8 g tannic acid in 80 ml water was then added, followed by addition of 200 ml of a 30 wt% solution, or 8.8 wt% of ethoxylated lanolin (Ethoxylan 100) in water. This mixture was stirred for 3 hours and then allowed to stand overnight at room temperature. The microcapsule precipitate was then centrifuged at 2700 rpm for 10 minutes to recover the microcapsules. Approximately 350 ml of non-agglomerated microcapsules that contained 16% to 20% by wet weight deet were obtained (about 60% by dry weight). The yield of microencapsulated deet was approximately 80%.

Example 3

30 g gelatin (Type 2503) was dissolved in 440 ml water at room temperature. A solution of 5.4 g stearic acid as a coacervation adjuvant in 157.5 ml deet was emulsified in the gelatin solution, using a blender (Model 31BL92, Dynamics Corp. of America, New Hartford, Connecticut) at room temperature. This emulsion was then evacuated for 20 minutes with continuous stirring, and was then added to a stirred solution of 20 g gum arabic (G-85) in 360 ml water at 45° C. Stirring was continued and the temperature was reduced to 19° C. over a three-hour period. 540 ml of a 30 wt% solution, or 12 wt%, of ethoxylated lanolin (Ethoxylan 100) in water was then added over a 20-minute period. 4.5 ml of 50 vol% glutaraldehyde and 0.3 ml of 36 vol% formaldehyde were then added, and the temperature was raised to 35° C. over a one-hour period with continuous stirring. The solution was then allowed to stand overnight at room temperature. The microcapsule precipitate was then centrifuged at 3000 rpm for 30 minutes to recover the microcapsules. Approximately 390 g of non-agglomerated microcapsules that contained 30% by wet weight deet were obtained (about 70% by dry weight). The yield of microencapsulated deet was approximately 75%.

Example 4

Example 1 was repeated with the exception that the solution of ethoxylated lanolin was not added. Severe agglomeration occurred, resulting in gelation of the entire solution, despite rapid stirring.

Example 5

Microcapsules obtained from Example 3 were mixed with a 47.5 wt% aqueous solution of a copolymer of methyl vinyl ether and maleic anhydride (Gantrez AN-119, GAF Corp., New York, New York), which functioned as a pharmaceutical vehicle, in a ratio of 91 parts microcapsules to 9 parts Gantrez AN-119 solution. The resulting cream was applied to human skin, and the amount of deet remaining on the skin was measured over a period of 12 hours. After the first two hours, 40% of the original amount of deet remained on the skin, after six hours, 20% remained, and after 10 hours 15% remained. In each case, the amount of deet remaining on the skin was the amount that could be recovered by rinsing the skin with alcohol. Laboratory testing of this formulation on rabbits against mosquitoes confirmed a long-lasting efficacy of more than eight hours.

The terms and expressions which have been employed in the foregoing specification are used therein as terms of description and not of limitation, and there is no intention, in the use of such terms and expressions of excluding equivalents of the features shown and described or portions thereof, it being recognized that the scope of the invention is defined and limited only by the claims which follow.

What is claimed is:

1. In a complex coacervation process for microencapsulating a core ingredient that is partially soluble in the walls of microcapsules comprising the steps of
    (a) forming an emulsion of said core ingredient in an aqueous solution of a first ionizable colloid,
    (b) forming an aqueous solution of a second ionizable colloid of opposite electrical charge to that of said first ionizable colloid,
    (c) forming a mixture by combining the emulsion of step (a) with the aqueous solution of step (b),
    (d) cooling said mixture of step (c) to cause gelation of microcapsule walls around droplets of said core ingredient, and
    (e) hardening said microcapsule walls, the improvement comprising the steps of
        (1) forming a coacervation adjuvant/core ingredient mixture prior to step (a) by mixing with said core ingredient a coacervation adjuvant selected from the group consisting of an ionizable colloid, an ionic surfactant and an ionizable long-chain organic compound,
        (2) substituting the coacervation adjuvant/core ingredient mixture formed in step (1) for the core ingredient of step (a), and
        (3) between steps (d) and (e), adding from 5 to 20% by weight of a water-soluble wax derivative selected from the group consisting of derivatives of any of lanolin, carnauba, beeswax, paraffin, polyether-esters and chlorinated naphthalenes, all of said steps being conducted without pH adjustment, without the addition of an inorganic salt, without dilution, and without phase inversion.

2. The process of claim 1 wherein the core ingredient is deet.

3. The process of claim 1 wherein the core ingredient is deet, the first and second colloids are selected from the group consisting of gelatin and gum arabic, and the water-soluble wax derivative is ethoxylated lanolin.

4. The process of claim 1 wherein said microcapsule walls are hardened by the addition of at least one hardening agent selected from the group consisting of tannic acid and aldehydes.

5. The product of the process of claim

6. A long-lasting mosquito repellent composition comprising a pharmaceutically acceptable vehicle and microcapsules, said microcapsules being made by, in the following order, the steps of
    (a) forming a coacervation adjuvant/mosquito repellent mixture by mixing a coacervation adjuvant selected from the group consisting of an ionizable colloid, an ionic surfactant and an ionizable long-chain organic compound with a mosquito repellent,
    (b) forming an emulsion by emulsifying said coacervation adjuvant/mosquito repellent mixture in an aqueous solution of a first ionizable colloid selected from the group consisting of gelatin, gum arabic, gum karaya, gum tragacanth, casein, carrageenan, and carboxymethylcellulose,
    (c) forming an aqueous solution of a second ionizable colloid of opposite electrical charge to that of the first ionizable colloid, said second ionizable colloid being selected from the group consisting of gelatin, gum arabic, casein, carrageenan, and carboxymethylcellulose,
    (d) forming a mixture by combining the emulsion of step (b) with the aqueous solution of step (c),
    (e) cooling said mixture of step (d) to cause gelation of microcapsule walls around droplets of said mosquito repellent,
    (f) adding to said cooled mixture of step (e) from 5 to 20% by weight of a water-soluble wax derivative selected from the group consisting of derivatives of any of lanolin, carnauba, beeswax, paraffin, polyether-esters and chlorinated naphthalenes, and
    (g) hardening said microcapsules walls, all of said steps being conducted without pH adjustment, without the addition of an inorganic salt, without dilution, and without phase inversion.

7. The composition of claim 6 wherein the mosquito repellent is deet.

8. The composition of claim 6 wherein said microcapsule walls are hardened by the addition of at least one hardening agent selected from the group consisting of tannic acid and aldehydes.

* * * * *

UNITED STATES PATENT AND TRADEMARK OFFICE
CERTIFICATE OF CORRECTION

PATENT NO. : 4,808,408

DATED : February 28, 1989

INVENTOR(S) : Richard W. Baker

It is certified that error appears in the above-identified patent and that said Letters Patent is hereby corrected as shown below:

On the title page:

In the Abstract:

| | |
|---|---|
| Line 5 | Change "adjacent" to --adjuvant-- |
| Col. 1, line 31, | Change "premeability" to --permeability-- |
| Col. 1, line 54, | Change "highyield" to --high-yield-- |
| Col. 4, line 11, | Change "ws" to --was-- |
| Col. 6, line 15, | After "claim" insert --1--. |

Signed and Sealed this

Fourteenth Day of August, 1990

Attest:

HARRY F. MANBECK, JR.

Attesting Officer     Commissioner of Patents and Trademarks